(12) United States Patent
Krueger et al.

(10) Patent No.: US 6,899,105 B2
(45) Date of Patent: May 31, 2005

(54) AIRWAY IMPLANT CARTRIDGE AND KIT

(75) Inventors: Kurt David Krueger, Stacy, MN (US); Daniel Matthew Gelfman, Minneapolis, MN (US)

(73) Assignee: Restore Medical, Inc., St. Paul, MN (US)

( * ) Notice: Subject to any disclaimer, the term of this patent is extended or adjusted under 35 U.S.C. 154(b) by 18 days.

(21) Appl. No.: 10/665,760

(22) Filed: Sep. 19, 2003

(65) Prior Publication Data

US 2005/0061334 A1 Mar. 24, 2005

(51) Int. Cl.$^7$ ............................................. A61B 19/00
(52) U.S. Cl. ...................... 128/897; 128/848; 604/57
(58) Field of Search ................ 128/897–898, 128/848; 600/7–8, 12; 604/57–63, 15

(56) References Cited

U.S. PATENT DOCUMENTS

| | | | |
|---|---|---|---|
| 4,909,250 A | * | 3/1990 | Smith .......................... 606/117 |
| 4,946,035 A | * | 8/1990 | Grimm et al. .............. 206/366 |
| 5,284,161 A | | 2/1994 | Karell |
| 5,456,662 A | | 10/1995 | Edwards et al. |
| 5,514,131 A | | 5/1996 | Edwards et al. |
| 5,674,191 A | | 10/1997 | Edwards et al. |
| 5,718,702 A | | 2/1998 | Edwards |
| 5,792,067 A | | 8/1998 | Karell |
| 5,843,021 A | | 12/1998 | Edwards et al. |
| 5,988,171 A | | 11/1999 | Sohn et al. |
| 6,098,629 A | | 8/2000 | Johnson et al. |
| 6,250,307 B1 | | 6/2001 | Conrad et al. |
| 6,387,113 B1 | * | 5/2002 | Hawkins et al. ............ 606/219 |
| 6,431,174 B1 | | 8/2002 | Knudson et al. |
| 6,432,035 B1 | * | 8/2002 | Ravins et al. .................. 600/7 |
| 6,513,530 B2 | | 2/2003 | Knudson et al. |

(Continued)

FOREIGN PATENT DOCUMENTS

EP   1 039 859 B1   12/2003

OTHER PUBLICATIONS

Boudewyms, A. et al., "Temperature-controlled Radiofrequency Tissue Volume Reduction of the Soft Palate (Somnosplasty®) in the Treatment of Habitual Snoring: Results of a European Multicenter Trial," *Acta Otolaryngol*, vol. 120, pp. 981-985 (2000).

(Continued)

*Primary Examiner*—John P. Lacyk
(74) *Attorney, Agent, or Firm*—Merchant & Gould P.C.

(57) ABSTRACT

According to one aspect of the present invention, an apparatus and related kit are disclosed for treating an airway condition of a patient. A cartridge apparatus is disclosed for use in treating an airway condition of a patient and for use in combination with a handle sized to be hand-grasped by an operator and having an actuator mechanism to be selectively actuated by said operator. The cartridge includes a implant of biocompatible material sized to be embedded within a tissue of the airway. A needle has a distal tip for penetrating into the tissue. The needle has an axially extending bore. The implant is disposed within the bore at the distal tip. The cartridge has a proximal end adapted to be coupled to the handle for the implant to be ejected from the distal tip upon actuation of the actuator. The kit of the invention includes a container including a plurality of such cartridges.

27 Claims, 9 Drawing Sheets

U.S. PATENT DOCUMENTS

| | | |
|---|---|---|
| 6,523,542 B2 | 2/2003 | Knudson et al. |
| 6,530,896 B1 * | 3/2003 | Elliott .................. 604/60 |
| 6,578,580 B2 | 6/2003 | Conrad et al. |
| 6,626,916 B1 * | 9/2003 | Yeung et al. ............ 606/139 |

OTHER PUBLICATIONS

Brietzke, S. et al., "Injection snoreplasty: How to treat snoring without all the pain and expense,"*Otolaryngology-Head and Neck Surgery*, vol. 124, No.5, pp. 503-510 (May 2001).

Cole, P. et al., "Snoring: A Review and a Reassessment:"*The Journal of Otolaryngology*, vol. 24, No. 5, pp. 303-306 (1995).

Coleman, S. et al., "Midline radiofrequency tissue reduction of the palate for bothersome snoring and sleep-disordered breathing: A clinical trial,"*Otolaryngology-Head and Neck Surgery*, vol. 122, No. 3, pp. 387-394 (Mar. 2000).

Harries, P. et al., "Review Article, The surgical treatment of snoring,"*The Journal of Laryngology and Otology*, vol. 110, pp. 1105-1106 (Dec. 1996).

Huang, L. et al., "Biomechanics of snoring,"*Endeavour*, vol. 19, No. 3, pp. 96-100 (1995).

LaFrentz et al., "Palatal Stiffening Techniques for Snoring in a Novel Canine Model,"*Abstracts of the Twenty-Second Annual Mid Winter Research Meeting of the Association for Research in Otolaryngology*, Abstract No. 499, vol. 22, p. 125-126 (Feb. 13-18, 1999).

Lorenz, C., "If he Snores-what can you do about it,"*Today's Woman*, 2 pgs. (Jul. 1948).

Parker, J., "Clinical Scientific Feature, An Overview of Snoring and Obstructive Sleep Apnea, Part One: Evaluation and Diagnosis,"*Northwest Dentistry*, pp. 17-22 (Jan.-Feb. 1995).

Schwartz, R. et al., "Effects of electrical stimulation to the soft palate on snoring and obstructive sleep apnea,"*The Journal of Prosthetic Dentistry*, vol. 76, No. 3, pp. 273-281 (Sep. 1996).

Wiltfang, J. et al., "First results on daytime submandibular electrostimulation of suprahyoidal muscles to prevent nighttime hypopharyngeal collapse in obstructive sleep apnea syndrome,"*International Journal of Oral & Maxillofacial Surgery*, vol. 28, pp. 21-25 (1999).

* cited by examiner

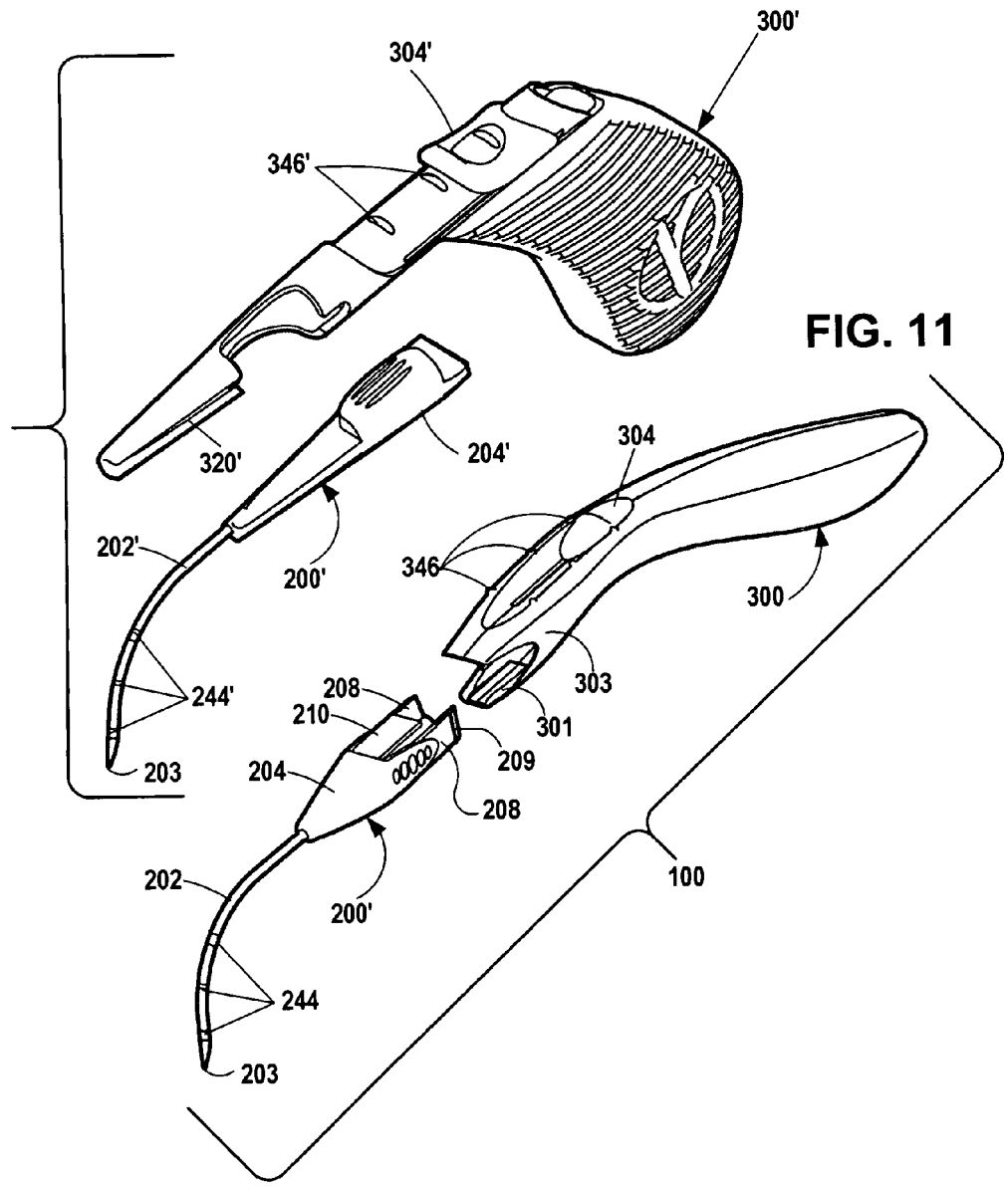

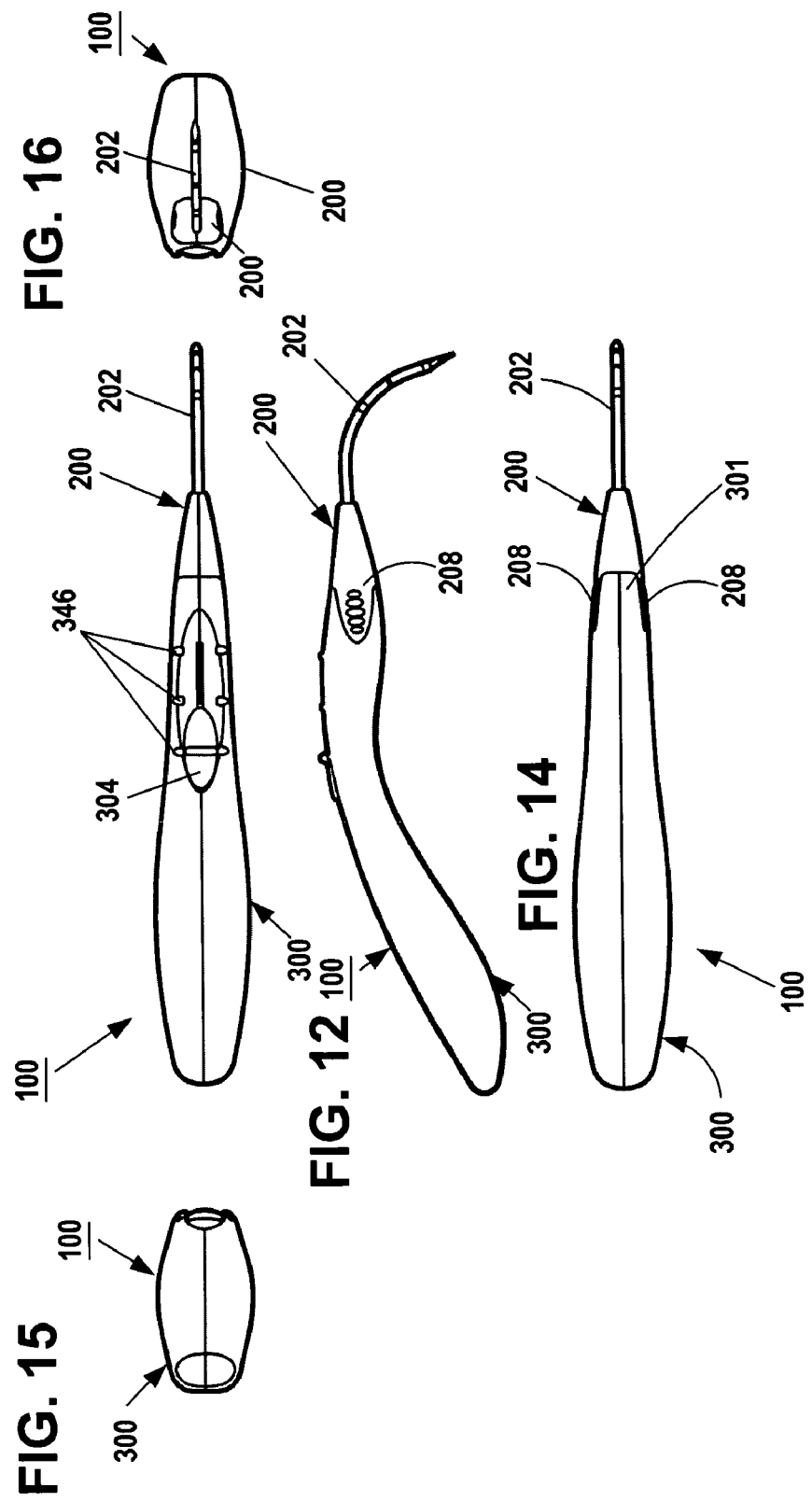

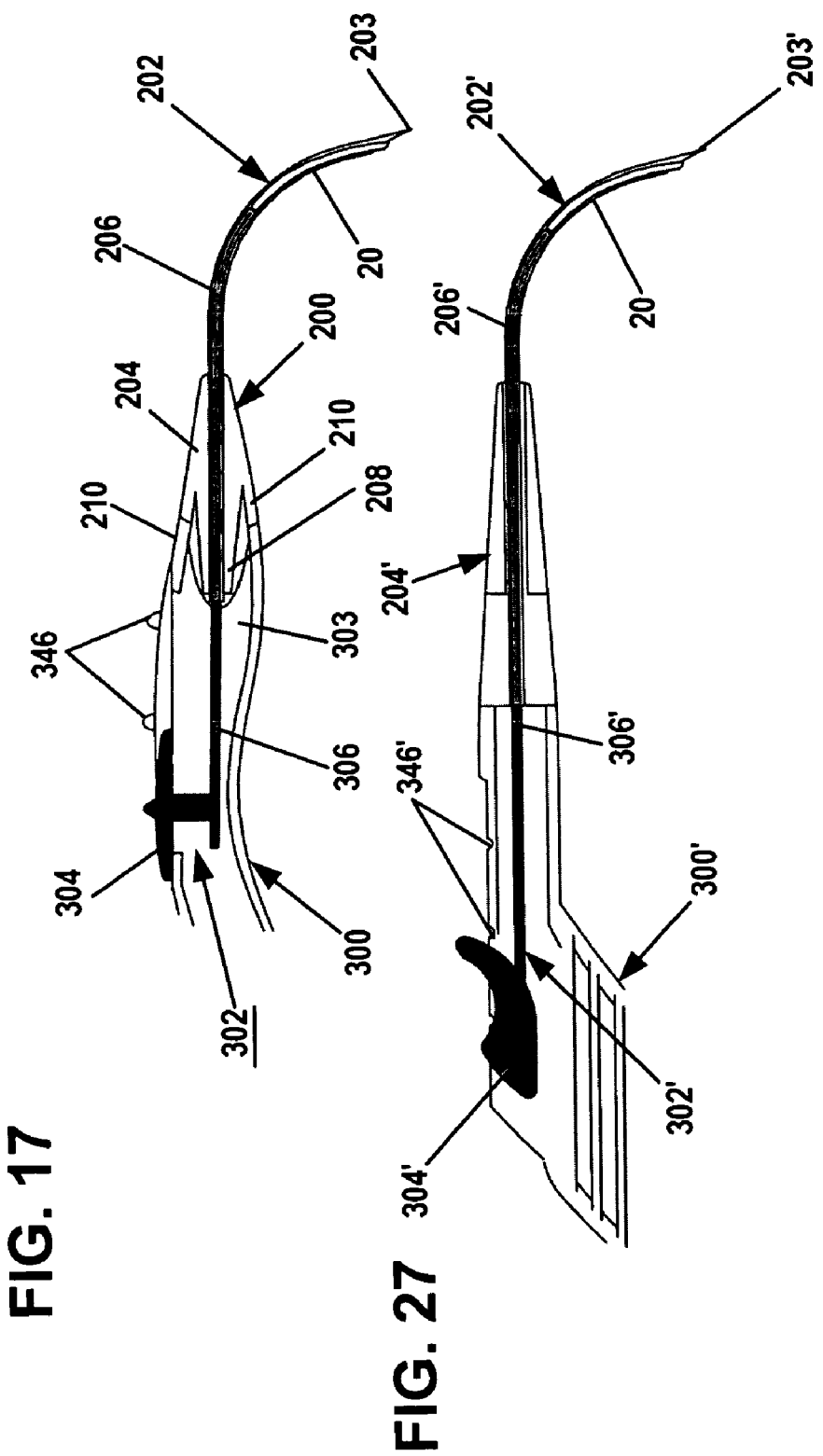

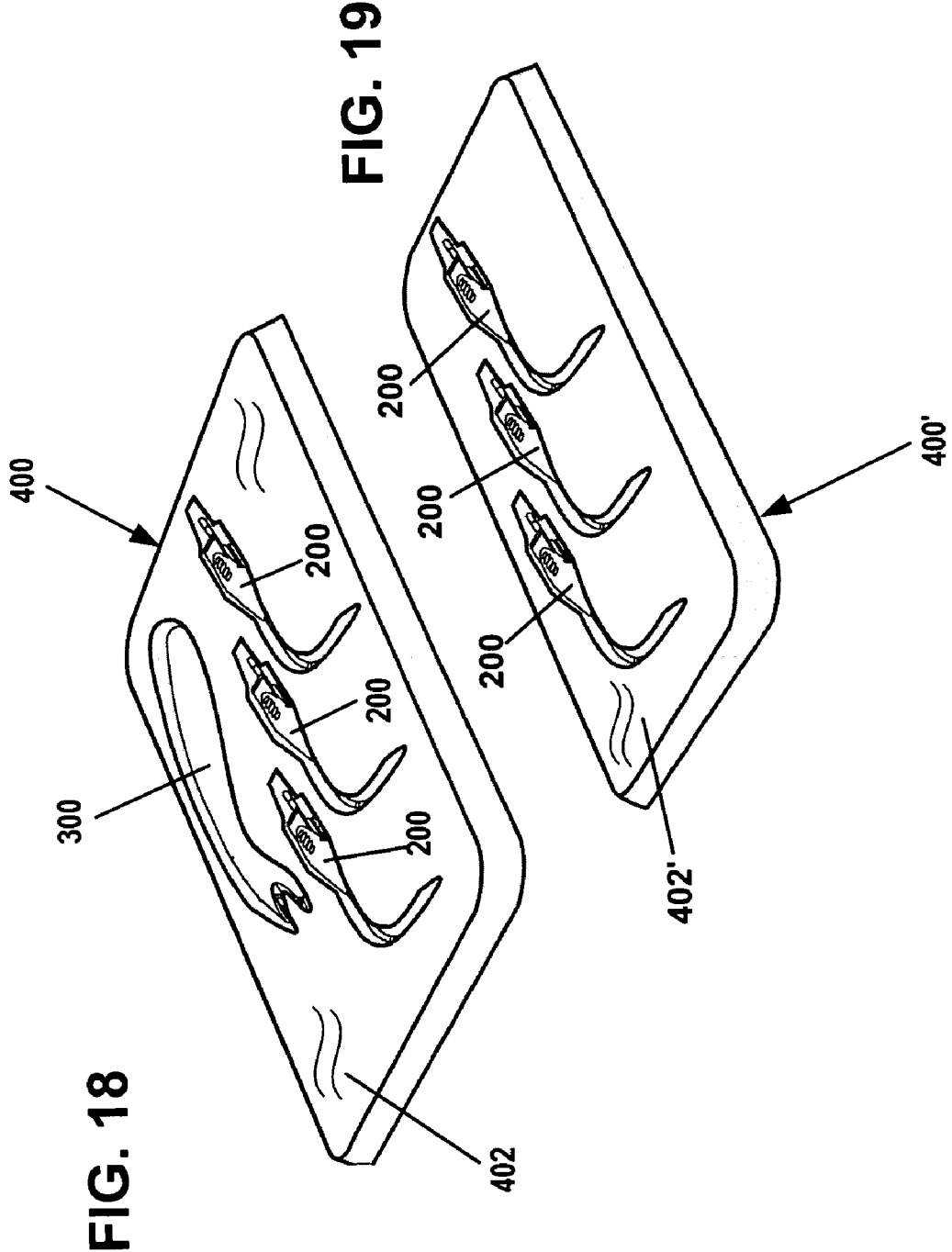

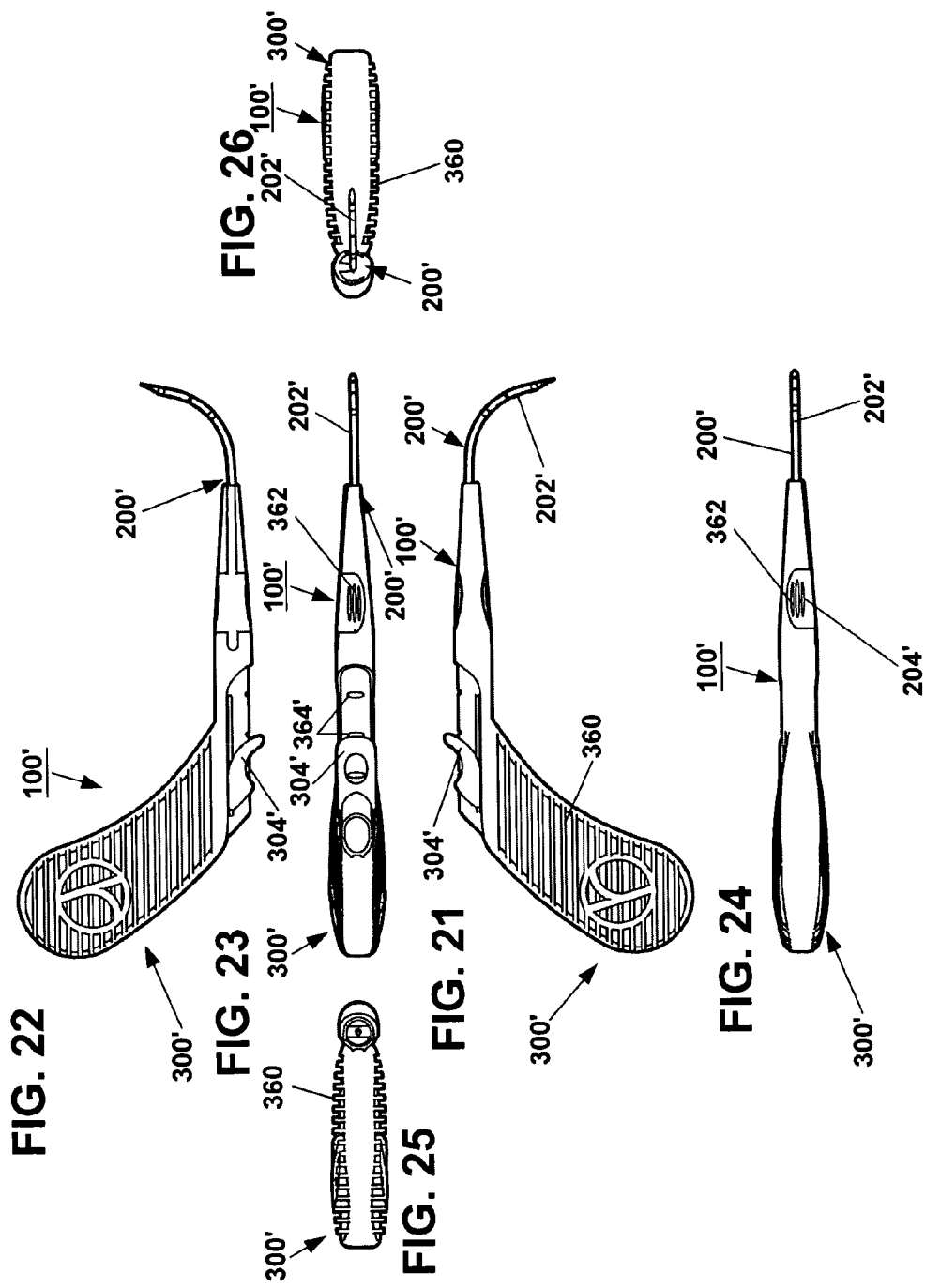

AIRWAY IMPLANT CARTRIDGE AND KIT

I. BACKGROUND

1. Field of the Invention

This invention is directed to an apparatus for treating an airway condition of a patient. More particularly, this invention is directed to an apparatus and related kit of a cartridge for connection to a handle for delivering an implant into tissue of a patient's airway.

2. Description of the Prior Art

Airway conditions such as snoring and obstructive sleep apnea (OSA) have received increased scientific and academic attention. One publication estimates that up to 20% of the adult population snores habitually. Huang, et al., "Biomechanics of Snoring", *Endeavour*, p. 96–100, Vol. 19, No. 3 (1995). Snoring can be a serious cause of marital discord. In addition, snoring can present a serious health risk to the snorer. In 10% of habitual snorers, collapse of the airway during sleep can lead to obstructive sleep apnea syndrome. Id.

Notwithstanding numerous efforts to address snoring and sleep apnea, effective treatments have been elusive. Such treatment may include mouth guards or other appliances worn by the snorer during sleep. However, patients find such appliances uncomfortable and frequently discontinue use (presumably adding to marital stress).

Electrical stimulation of the soft palate has been suggested to treat snoring and obstructive sleep apnea. See, e.g., Schwartz, et al., "Effects of electrical stimulation to the soft palate on snoring and obstructive sleep apnea", *J. Prosthetic Dentistry*, pp. 273–281 (1996). Devices to apply such stimulation are described in U.S. Pat. Nos. 5,284,161 and 5,792,067. Such devices are appliances requiring patient adherence to a regimen of use as well as subjecting the patient to discomfort during sleep. Electrical stimulation to treat sleep apnea is discussed in Wiltfang, et al., "First results on daytime submandibular electrostimulation of suprahyoidal muscles to prevent night-time hypopharyngeal collapse in obstructive sleep apnea syndrome", *International Journal of Oral & Maxillofacial Surgery*, pp. 21–25 (1999).

Surgical treatments have been employed. One such treatment is uvulopalatopharyngoplasty. In this procedure, so-called laser ablation is used to remove about 2 cm of the trailing edge of the soft palate thereby reducing the soft palate's ability to flutter between the tongue and the pharyngeal wall of the throat. The procedure is frequently effective to abate snoring but is painful and frequently results in undesirable side effects. Namely, removal of the soft palate trailing edge comprises the soft palate's ability to seal off nasal passages during swallowing and speech. In an estimated 25% of uvulopalatopharyngoplasty patients, fluid escapes from the mouth into the nose while drinking. Huang, et al., supra at 99. Uvulopalatopharyngoplasty (UPPP) is also described in Harries, et al., "The Surgical treatment of snoring", *Journal of Laryngology and Otology*, pp. 1105–1106 (1996) which describes removal of up to 1.5 cm of the soft palate. Assessment of snoring treatment is discussed in Cole, et al., "Snoring: A review and a Reassessment", *Journal of Otolaryngology*, pp. 303–306 (1995).

Novel treatments for snoring and sleep apnea are described in various patents commonly assigned with the present application. These include U.S. Pat. No. 6,250,307 to Conrad et al. dated Jun. 26, 2001 which describes (along with other embodiments) elongated implants for placement in the soft palate. In one embodiment, three such implants are placed in the soft palate. U.S. Pat. No. 6,578,580 to Conrad et al. dated Jun. 17, 2003 describes a needle (which may have a perforated distal tip) for delivery of an implant. The implant may be preloaded into the needle. In U.S. Pat. No. 6,523,542 to Metzger et al. dated Feb. 25, 2003, an implant is described as a sheet of felt or similar material delivered through a needle. U.S. Pat. No. 6,513,530 to Knudson et al. dated Feb. 4, 2003 describes the implant as a braid with welded ends near frayed ends. U.S. Pat. No. 6,431,174 to Knudson et al. dated Aug. 13, 2002 describes use of microbeads as implants as well as describing placement of implants in a pharyngeal wall or nasal area as well as a soft palate.

When placing implants in the tissue of a patient's airway (i.e., in soft palate, nasal or pharyngeal wall tissue), it may often be desirable to place more than one such implant (e.g., the three parallel longitudinal implants shown in the soft palate in the aforementioned U.S. Pat. No. 6,250,307). Delivery systems for such implants should accommodate the need for multiple implants, the need to protect the implant and delivery system from damage, facilitate ease and accuracy of implant placement and to maintain sterility. Also, such systems should be cost effective and minimize waste. It is an object of the present invention to provide such a delivery system.

II. SUMMARY OF THE INVENTION

According to one aspect of the present invention, an apparatus and related kit are disclosed for treating an airway condition of a patient. A cartridge apparatus is disclosed for use in treating an airway condition of a patient and for use in combination with a handle sized to be hand-grasped by an operator and having an actuator mechanism to be selectively actuated by said operator. The cartridge includes a implant of biocompatible material sized to be embedded within a tissue of the airway. A needle has a distal tip for penetrating into the tissue. The needle has an axially extending bore. The implant is disposed within the bore at the distal tip. The cartridge has a proximal end adapted to be coupled to the handle for the implant to be ejected from the distal tip upon actuation of the actuator. The kit of the invention includes a container including a plurality of such cartridges.

III. BRIEF DESCRIPTION OF THE DRAWINGS

FIG. 11 is a top, front and left side perspective view of a preferred embodiment of a combined handle and cartridge of the present invention shown in exploded form with the cartridge separated from the handle;

FIG. 12 is a right side elevation view of the combined handle and cartridge of FIG. 11 (with the opposite side being substantially identical);

FIG. 13 is a top plan view of the combined handle and cartridge of FIG. 11;

FIG. 14 is a bottom plan view of the combined handle and cartridge of FIG. 11;

FIG. 15 is a rear end elevation view of the combined handle and cartridge of FIG. 11;

FIG. 16 is a front-end elevation view of the combined handle and cartridge of FIG. 11;

FIG. 17 is a side-sectional view of an assembled handle and cartridge of FIG. 11 showing internal components;

FIG. 18 is a top, front and side perspective view of a kit according to the present invention including a handle and a plurality of cartridges contained within a sterile container;

FIG. 19 is a top and side perspective view of a kit according to the present invention including a plurality of cartridges contained within a sterile container;

FIG. 20 is a view similar to that of FIG. 11 showing an alternative embodiment of handle and cartridge (shown exploded in FIG. 20);

FIG. 21 is a right side elevation view of the combined handle and cartridge of FIG. 20;

FIG. 22 is a left side elevation view of the combined handle and cartridge of FIG. 20;

FIG. 23 is a top plan view of the combined handle and cartridge of FIG. 20;

FIG. 24 is a bottom plan view of the combined handle and cartridge of FIG. 20;

FIG. 25 is a rear end elevation view of the combined handle and cartridge of FIG. 20;

FIG. 26 is a front end elevation view of the combined handle and cartridge of FIG. 11; and FIG. 27 is a side-sectional view of an assembled handle and cartridge of FIG. 20 showing internal components.

IV. DESCRIPTION OF THE PREFERRED EMBODIMENT

With reference now to the various drawing figures, in which identical elements are numbered identically throughout, a detailed description of a preferred embodiment of the present invention will now be provided. The teachings of the following U.S. patents are incorporated herein by reference: U.S. Pat. No. 6,250,307 to Conrad et al. dated Jun. 26, 2001; U.S. Pat. No. 6,578,580 to Conrad et al. dated Jun. 17, 2003; U.S. Pat. No. 6,523,542 to Metzger et al. dated Feb. 25, 2003; U.S. Pat. No. 6,513,530 to Knudson et al. dated Feb. 4, 2003; and U.S. Pat. No. 6,431,174 to Knudson et al. dated Aug. 13, 2002.

A. Physiology Background

Figure 1:
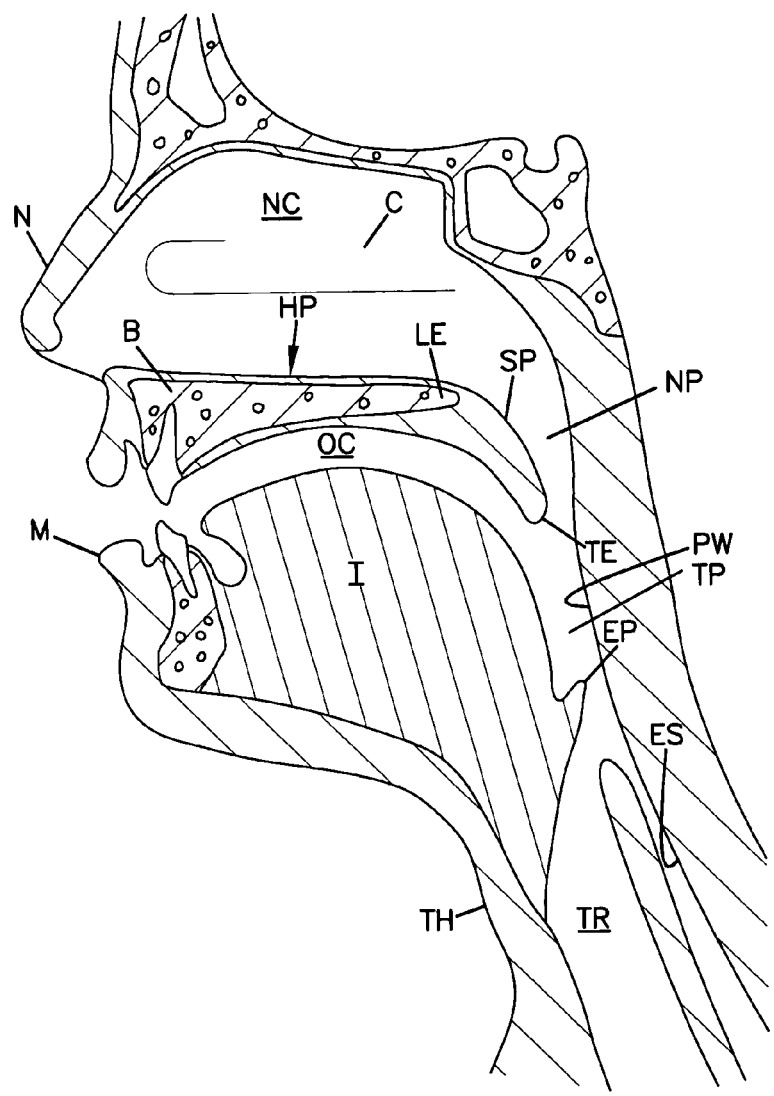
FIG. 1 shows, in cross-section, a naso-pharyngeal area of an untreated patient.
Figure 2:
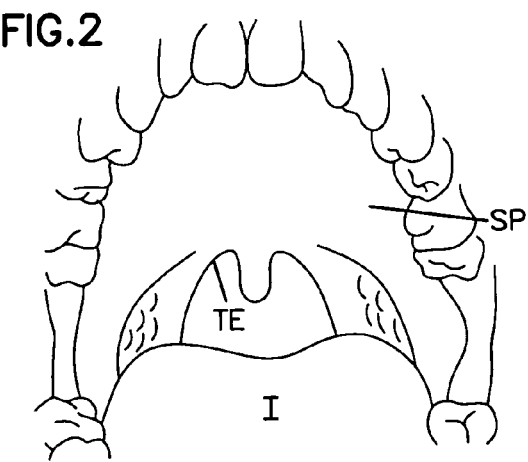
FIG. 2 shows a soft palate viewed through an open mouth of the untreated patient of FIG. 1.

FIG. 1 shows, in cross-section, a naso-pharyngeal area of an untreated patient. FIG. 2 shows a soft palate SP viewed through an open mouth of the untreated patient. FIG. 1 shows the nose N, mouth M and throat TH. The tongue T is shown in an oral cavity OC of the mouth. A hard palate HP (containing a bone B) separates the oral cavity OC from the nasal cavity NC. The nasal concha C (soft tissue which defines, in part, the nasal sinus—not shown) resides in the nasal cavity NC.

The soft palate SP (a muscle activated soft tissue not supported by bone) depends in cantilevered manner at a leading end LE from the hard palate HP and terminates at a trailing end TE. Below the soft palate SP, the pharyngeal wall PW defines the throat passage TP. A nasal passage NP connects the nasal cavity NC to the pharyngeal wall PW. Below an epiglottis EP, the throat passage TP divides into a trachea TR for passing air to the lungs and an esophagus ES for passing food and drink to the stomach.

The soft palate SP is operated by muscles (not separately shown and labeled) to lift the soft palate SP to urge the trailing edge TE against the rear area of the pharyngeal wall PW. This seals the nasal cavity NC from the oral cavity OC during swallowing. The epiglottis EP closes the trachea TR during swallowing and drinking and opens for breathing.

For purposes of this disclosure, the nasal cavity NC, oral cavity OC and throat passage TP are collectively referred to as the naso-pharyngeal area (or airway) of the patient with the area including the various body surfaces which cooperate to define the nasal cavity NC, oral cavity OC and throat passage TP. These body surfaces include outer surfaces of the nasal concha C, the upper and lower surfaces of the soft palate SP and outer surfaces of the pharyngeal wall PW. Outer surfaces means surfaces exposed to air. Both the upper and lower surfaces of the soft palate SP are outer surfaces.

Snoring can result from vibration of any one of a number of surfaces or structures of the naso-pharyngeal area. Most commonly, snoring is attributable to vibration of the soft palate SP. However, vibratory action of the nasal concha C and the pharyngeal wall PW can also contribute to snoring sounds. It is not uncommon for vibratory action from more than one region of the naso-pharyngeal area to contribute to snoring sounds. Sleep apnea can result from partial or full collapse of the naso-pharyngeal wall during sleep as well as having nasal and palatal contributions.

As indicated above, most of the present discussion will describe placing a stiffening implant in the soft palate SP, it will be appreciated the present invention is applicable to other regions of the naso-pharyngeal area including the nasal concha C and the pharyngeal wall PW. Also, it will be appreciated the present invention is applicable to airway conditions such as OSA or snoring and is not intended to be limited to snoring although this indication will be most frequently referenced for purpose of illustration of the invention. It will also be appreciated the present invention can be used with different types of implants (i.e., any of those referenced in the references incorporated by reference above) or any other implant which may be delivered from a needle.

The snoring sound is generated by impulses caused by rapid obstruction and opening of airways. Huang, et al., state the airway passage opening and closing occurs 50 times per second during a snore. Huang, et al., utilize a spring-mass model (FIG. 5) to illustrate oscillation of the soft palate in response to airflow (where the soft palate is the ball B of mass depending by a spring S from a fixed anchor A).

Figure 3:
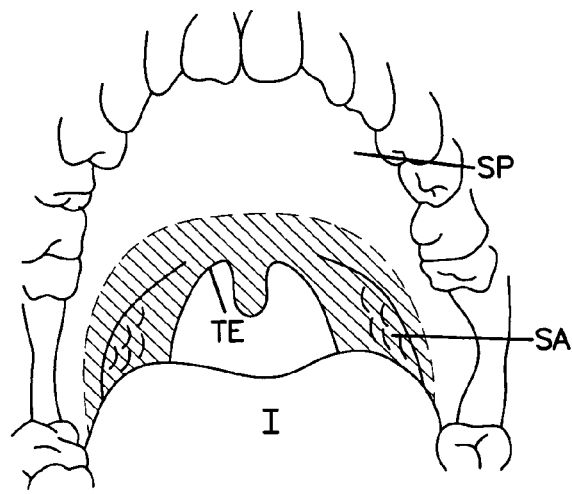
FIG. 3 is a front view of an interior of the mouth shown in FIG. 1 and showing an area to be ablated according to a first prior art surgical procedure.
Figure 4:
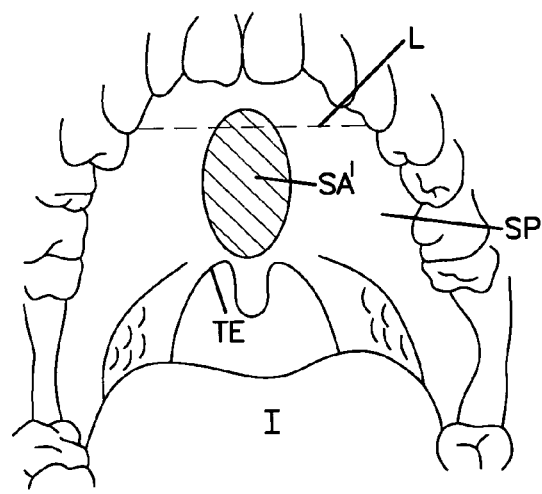
FIG. 4 is the view of FIG. 3 and showing an area to be scarred according to a second prior art surgical procedure.

A prior art technique for treating the soft palate is uvulopalatopharyngoplasty (UPPP). In UPPP, a trailing edge of the soft palate is removed. The shaded area SA in FIG. 3 shows the area of the trailing end TE of the soft palate SP to be removed during this procedure. Huang, et al., analogize the shortening of the soft palate SP in UPPP as effectively raising the critical airflow speed at which soft palate flutter will occur. An alternative procedure proposed by Huang, et al., reduces the flexibility of the soft palate SP through surface scarring which is asserted as affecting the critical flow speed. The shaded area SA' in FIG. 4 shows the area to be scarred by this alternate procedure. In FIG. 4, dashed line L shows the demarcation between the soft and hard palates.

Figure 5:
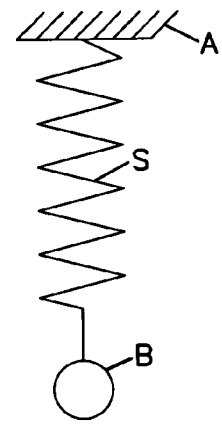
FIG. 5 is a schematic representation of a spring-mass system model of the soft palate.

Using the spring-mass model of FIG. 5 as a convenient model of the soft palate SP, the present invention is directed to a delivery system for a surgical implant for the soft palate SP to alter the elements of the model and thereby alter the dynamic response of the soft palate SP to airflow.

B. Disclosure of Commonly Assigned U.S. Patents

The aforementioned commonly assigned US patents (which have been incorporated herein by reference) describe a wide variety of airway implants for treating snoring or OSA. These patents are U.S. Pat. Nos. 6,250,307; 6,578,580; 6,523,542; 6,513,530 and 6,431,174.

In a presently preferred embodiment, the implant 20 is a braid of fibers 22. While a single type fiber could be used in implant 20, the implant can be formed of two or more different fibers braided or twisted together. For example, one fiber may be provided for encouraging fibrotic response. Such a fiber may be polyester or silk suture material. The other fiber may be a bio-resorbable fiber (e.g., bio-resorbable suture material which may include natural materials such as collagen or synthetic materials such as the PDS suture material). Alternatively, the other fiber may be a non-resorbable material such as polypropylene suture material to provide added stiffness to the implant.

Figure 6:
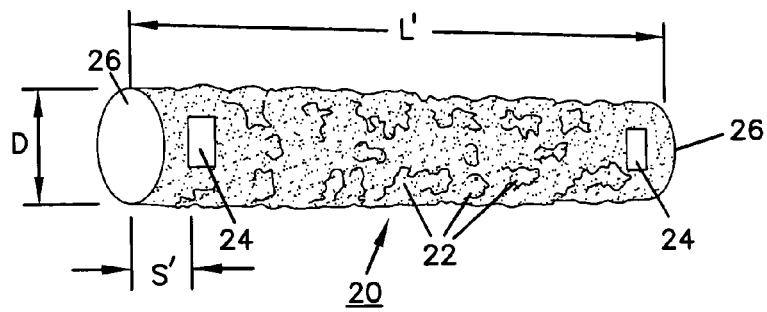
FIG. 6 is perspective view of an implant for use with the present invention.

In a preferred embodiment (shown in FIG. 6), the implant 20 is a composite braid of both air-textured and non-air-textured yarns of polyester formed in a braid of about 2 mm in diameter (D) and 18 mm in length (L'). Welds 24 are formed near the ends 26 of the implant 20 to bond the fibers 22. The welds 24 are spaced from the ends 26 by a spacing S' so that the fibers 22 in the spacing are free to fray and present a fluffier area for tissue in-growth. The implant 20 is fibrosis inducing to induce a fibrotic response of tissue following implantation. An implant having the foregoing characteristics is more fully described in the aforementioned U.S. Pat. No. 6,513,530.

Figure 7:
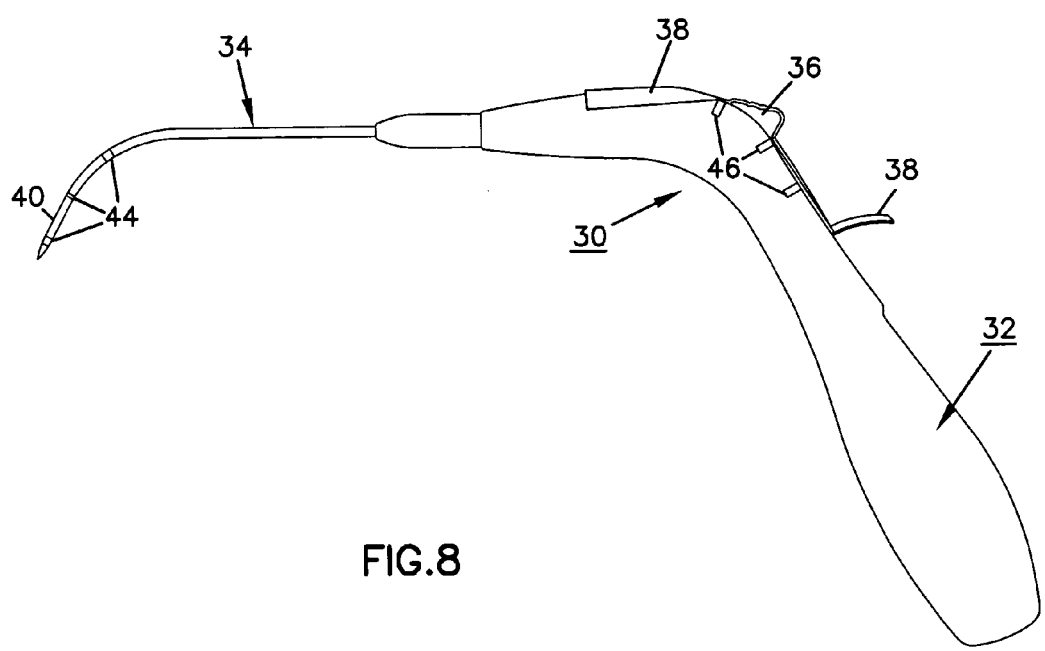
FIG. 7 is a side elevation view of a prior delivery tool for delivery of the implant of FIG. 6 into the soft palate of a patient.
Figure 8:
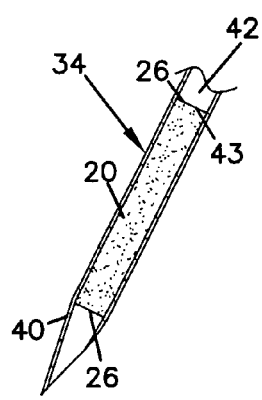
FIG. 8 is a side-sectional view of a distal tip of the tool of FIG. 7 cut-away to reveal the implant of FIG. 6 preloaded into the distal tip of the tool.
Figure 9:
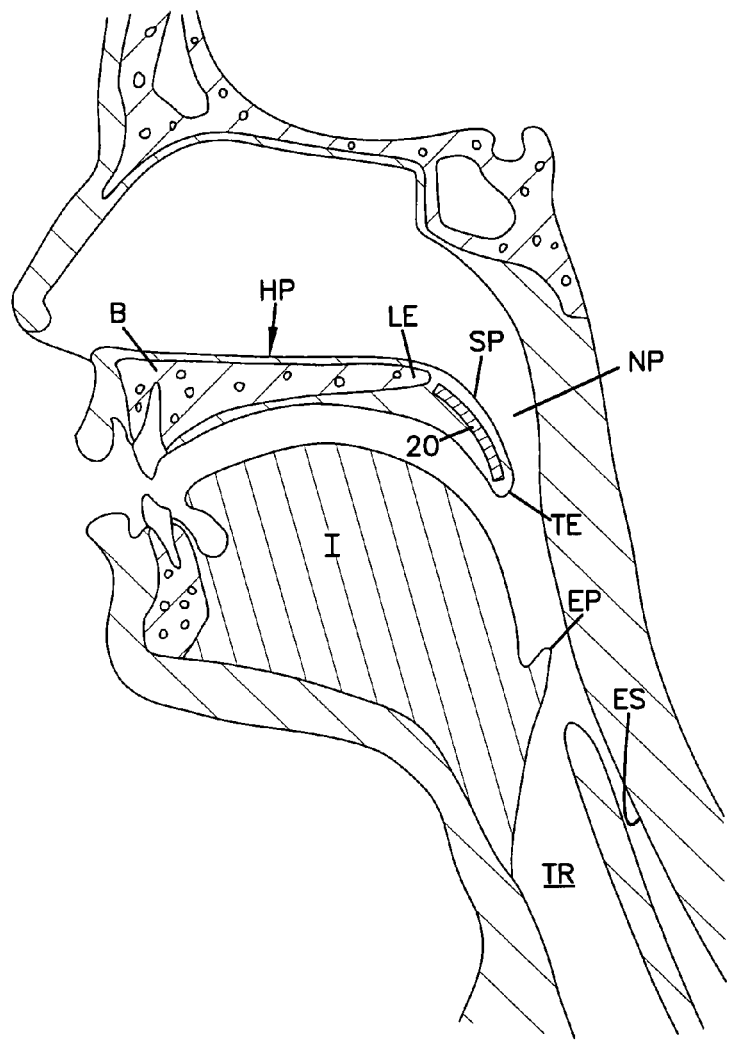
FIG. 9 is the view of FIG. 1 with the soft palate containing the implant of FIG. 6.
Figure 10:
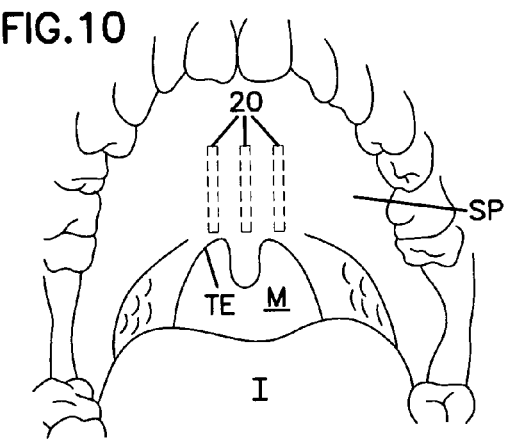
FIG. 10 is the view of FIG. 2 showing three implants of the type of FIG. 6 in the soft palate.

FIGS. 7 and 8 show a prior delivery tool 30 for placing the implant 20 in the soft palate SP. FIGS. 9 and 10 illustrate the desired placement of the implant 20 in the soft palate SP. As shown in FIG. 10, three implants are preferably placed in the soft palate SP. One at the soft palate midline and one each on opposite sides of the midline about 5 mm from the midline.

The delivery tool 30 includes a handle 32 and a needle 34 permanently secured to the handle 32. The handle 32 is designed to be hand-grasped in a pistol-grip manner with a sliding thumb switch 36 positioned to oppose the operator's thumb (not shown) when the handle 32 is grasped. A removable tape 38 covers the thumb switch 36 during shipping and storage to prevent undesired movement of the thumb switch 36. The distal tip 40 of the needle 34 is bent to permit ease of placement of the tip 40 in the soft palate SP without interference of the tool 30 with the patient's teeth or hard palate.

The needle 34 is connected to the thumb switch 36 through linkage (not shown) contained within the handle 32 such that the needle retracts to the right (i.e., moves rearward into the handle 32) as the thumb switch is slid downwardly on the handle 32. Directions "right", "rearward" and "down" are with reference to the orientation shown in FIG. 7.

The distal tip 40 of needle 34 has a bevel ground for piercing tissue of the soft palate. The needle 34 is hollow and carries the implant 20 in sliding close tolerance at the distal tip 40.

An obturator or rod 42 is positioned in the needle 34 between the implant 20 and the handle 32. The obturator 42 is secured to the handle 32 so that is does not retract as the needle retracts. Therefore, as the needle 34 retracts, the needle 34 slides over the fixed-place obturator 42. The distal end 43 of the obturator 42 butts against the implant 20. This prevents the implant 20 from moving with the needle 34 as the needle 34 retracts. As a result, the retracting needle 34 exposes the implant 20.

The implant 20 is carried by the needle 34 to a desired implant site within the soft palate SP. At the desired site, the implant 20 is deployed by retracting the needle 34. Retraction is performed by retracting back on thumb switch 36. Retraction of the needle relative to the handle causes the obturator 42 to dispel the implant 20 from the needle 34. The aforementioned U.S. Pat. No. 6,578,580 describes a retracting needle and stationary rod to deploy an implant in the soft palate. That patent also describes a pre-loaded implant.

The needle has markings 44 to provide indication to an operator of depth of penetration of the needle tip 40 in tissue and location of the implant 20. Corresponding markings 46 are placed on the handle 32 to illustrate the degree of needle retraction and implant exposure relative to sliding movement of the thumb switch 36.

The implant 20 is pre-loaded into the needle 34. The needle 34 is non-removably secured to the handle 32 and all components are delivered in a sterile package. Such packaged implant and its delivery system are the subject of 510k clearance (K01 1723) from the U.S. Food and Drug Administration and CE Mark certification (CE 66447) from BSI Product Services indicated for use with the treatment of socially disruptive snoring. The product is sold by Restore Medical Inc., St. Paul, Minn., USA—assignee of the present application.

C. Apparatus and Kit of the Present Invention

With reference to FIGS. 11–17, the present invention is shown in a first preferred embodiment. The delivery system 100 of the present invention includes a cartridge 200 and a handle 300. As will be more fully described, the cartridge 200 is separate from the handle 300 and may be attached to or detached from the handle 300 at the option of an operator.

The cartridge 200 includes a hollow needle 202 and an implant 20. Since, in a preferred embodiment, the implant 20 is identical to that shown in FIG. 6 it is identically numbered in views of FIG. 17. As described above, the implant 20 is a braid of fibrosis-inducing fibers. The implant 20 may have a diameter slightly larger than the interior diameter of the needle such that the implant may expand upon ejection from the needle. As described in the aforementioned patents (e.g., U.S. Pat. No. 6,250,307), the implant 20 is adapted to alter a dynamic response of airway tissue following placement of the implant in the tissue.

As will be more fully described, the cartridge 200 has a cartridge coupling 204 at the proximal end of the needle 202. An obturator 206 is slidably disposed within the bore of the needle 202. The implant 20 is placed at the distal tip 203 of the needle 202. The obturator 206 is sized for a distal end of the obturator 206 to oppose and abut a proximal end of the implant 20. The length of the obturator 206 is selected for a proximal end of the obturator 206 to be flush with a proximal end of the needle 202 at the cartridge coupling 204.

The handle 300 includes a driver mechanism 302. The driver mechanism 302 includes a thumb switch 304 slidably mounted on the handle 300. The thumb switch 304 moves forward from a lock position to a deploy position with the throw distance between the positions being greater than the length L' of the implant 20.

The driver mechanism 302 also includes a push rod 306 contained within the handle 200. The push rod 306 is connected to the thumb switch 304 to move with it as the switch 304 is moved between the lock and deploy positions.

The handle 300 has a distal end 301 with a predetermined geometry. The cartridge coupling 204 has a mating geometry selected to couple with the predetermined geometry of the handle 300. In the embodiment of FIGS. 11 and 17, the mating surfaces of the cartridge coupling 204 includes sidewalls 208 and top and bottom walls 210. The sidewalls 208 are flexible and include an end barb 209 to releasable detach with indents on interior surfaces of the handle sidewalls 303. The walls 208, 210 of the cartridge 200 align with the walls of the handle 300 so that the proximal end of the cartridge coupling 204 may be slid into mating engagement with the distal end 301 of the handle 300 with the barbs 209 releasably latching the cartridge 200 to the handle 300.

When positioned as described above, the cartridge 200 is coupled to the handle 300 with the proximal end of the obturator 206 exposed to and aligned with a distal end of the push rod 306. The push rod 306 is aligned and sized with the needle bore to advance into the needle 202 and abut and push the obturator 206 when the cartridge coupling 204 is connected to the handle 300 and when the thumb switch 304 is moved forward. This action causes the obturator 206 to move forward toward the distal tip 203 of the needle 202. Since the thumb switch throw is greater than the implant length (plus any spacing between the obturator 206 and implant 20 and between the obturator 206 and push rod 306), the complete throw of the switch 304 ejects the implant 20 from the distal tip 203. When the thumb switch 304 is returned to the lock position, the push rod 306 is retracted from the needle 202 and the cartridge 200 may be removed from the handle 200 by squeezing sidewalls 208 inwardly to release the barbs 209 from the detents on sidewalls 303.

It will be noted that unlike the design of FIG. 7, the design of FIGS. 11–17 moves the obturator 206 while holding the needle 202 fixed relative to the handle 300. Similar to FIG. 7, both needle 202 and handle 300 have markings 244, 346, respectively, to assist an operator in placement. The obturator 206 is part of the cartridge 200 and moves with the needle 202 when the cartridge 200 is disconnected from the handle 300.

In practice, a plurality of implants 20 are normally preferred to be placed in patient's tissue for each office visit. FIG. 18 shows a kit including a handle 300 and three cartridges 200 contained within a package or container 400 (with clear cover 402) which (together with the handle 300 and cartridges 200) is sterilized. In FIG. 18, the cartridges 200 are all disconnected from the handle 300. One of the cartridges 200 could be pre-connected to the handle 200 for convenience. FIG. 19 shows an alternative kit where three cartridges 200 without a handle 300 are packed as a plurality of cartridges 200 in a single container 400' (with clear cover 402') with the container 400' and cartridges 200 sterilized.

In the embodiment of FIGS. 11–17, the cartridge 200 is coupled to the handle 300 by axially sliding the cartridge coupling 204 toward the distal end 303 of the handle. FIGS. 20–27 illustrate an alternative embodiment where the coupling 204' is moved sideways into the distal end 303' of the handle 300'. Elements in common between the embodiments of FIGS. 11–17 and FIGS. 20–27 are numbered identically with the addition of an apostrophe to distinguish the embodiments and such elements need not be separately described. In FIG. 20, the distal tip 303' of the handle has a side slot 320' to receive the mating geometry of the cartridge coupling 204'. The handle 300' includes a textured gripping surface including ribs 360. In the depicted embodiments, the ribs 360 extend in a direction generally parallel to the direction of movement of the thumb switch 304'. The cartridge 200' also includes gripping elements 362 provided on the top and bottom sides of the coupling 204'.

The present invention has been described in a first preferred embodiment for delivery of a braided implant into tissue of the soft palate to treat an airway condition such as obstructive sleep apnea or socially disruptive snoring. It will be appreciated the present invention covers a wide variety of implants (e.g., instead of the braided implant, the implant may be a bolus of particulate material as described in U.S. Pat. No. 6,431,174 or a sheet of fibrosis-inducing material as described in U.S. Pat. No. 6,523,542). Also, the invention is readily adapted through change of needle size and curvature to permit placement of an implant in airway tissue other than the soft palate (e.g., placement in tissue of the nasal cavity or pharyngeal wall).

What is claimed is:

1. A cartridge apparatus for use in treating an airway condition of a patient and for use in combination with a handle sized to be hand-grasped by an operator and having an actuator to be selectively actuated by said operator, said cartridge comprising:
   an elongated implant of biocompatible material sized to be embedded within a tissue of said airway;
   a needle having a distal tip for penetrating into said tissue, said needle having an axially extending bore;
   at least one of needle marking on said needle near said distal tip and positioned to indicate a depth of penetration of said distal tip into a tissue and a location of said implant;
   said implant disposed within said bore at said distal tip;
   said cartridge having a proximal end adapted to be coupled to said handle for said implant to be ejected from said distal tip upon actuation of said actuator;
   at least one handle marking on said handle in proximity with said actuator, said handle markings corresponding to said needle marking and positioned to illustrate a degree of exposure of said implant from said distal tip in response to a movement of said actuator.

2. A cartridge according to claim 1 wherein said actuator includes a driver positioned to move upon actuation of said actuator, said cartridge further comprising:
   an obturator disposed for slideable movement within said bore of said needle;
   said obturator disposed to be moved by said driver toward said implant upon actuation of said actuator when said cartridge is coupled to said handle.

3. A cartridge according to claim 2 wherein:
   said obturator is carried within said bore of said needle for movement therewith when said cartridge is uncoupled from said handle.

4. A cartridge according to claim 2 wherein said bore is positioned relative to said proximal end for said driver to be slide-ably received within said bore when said cartridge is coupled to said handle.

5. A cartridge according to claim 1 wherein said handle has a handle coupling having a predetermined geometry, said cartridge further comprising:
   a cartridge coupling at said proximal end of said cartridge and having a mating geometry to mated with said predetermined geometry with said cartridge and handle aligned for said implant to be ejected from said distal tip upon actuation of said actuator.

6. A cartridge according to claim 5 further comprising a release for releasing said cartridge from said handle.

7. A cartridge according to claim 1 wherein said implant is adapted to alter a dynamic response of said tissue following placement of said implant in said tissue.

8. A cartridge according to claim 1 wherein said implant includes a material for promoting tissue in-growth into said implant following placement of said implant into said tissue.

9. A cartridge according to claim 1 wherein said implant is sized slightly greater than said bore for said implant to expand upon ejection from said bore.

10. A cartridge according to claim 8 wherein said implant is formed of multiple fibers including fibers of said material for promoting tissue in-growth.

11. A cartridge according to claim 10 wherein the multiple fibers are twisted together along a length of the implant with the fibers having terminal ends at opposite ends of the implant.

12. A cartridge according to claim 10 wherein the multiple fibers are braided together.

13. A cartridge according to claim 1 wherein said cartridge is contained within a sterile container.

14. A cartridge kit for use in treating an airway condition of a patient and for use in combination with a handle sized to be hand-grasped by an operator and having an actuator mechanism to be selectively actuated by said operator, at least one handle marking on said handle in proximity with said actuator, said cartridge kit comprising:
   a container;
   a plurality of cartridge contained within said container with each comprising:
      an implant of biocompatible material sized to be embedded within a tissue of said airway;
      a needle having a distal tip for penetrating into said tissue, said needle having an axially extending bore;
      said implant disposed within said bore at said distal tip;
      at least one of needle marking on said needle near said distal tip and positioned to indicate a depth of penetration of said distal tip into a tissue and a location of said implant, said needle marking corresponding to said handle marking;
      a proximal end adapted to be coupled to said handle for said implant to be ejected from said distal tip upon actuation of said actuator.

15. A cartridge kit according to claim 14 wherein said actuator includes a driver positioned to move upon actuation of said actuator, each of said cartridges further comprising:
   an obturator disposed for slideable movement within said bore of said needle;
   said obturator disposed to be moved by said driver toward said implant upon actuation of said actuator when said cartridge is coupled to said handle.

16. A cartridge kit according to claim 15 wherein:
   said obturator is carried within said bore of said needle for movement therewith when said cartridge is uncoupled from said handle.

17. A cartridge kit according to claim 15 wherein said bore is positioned relative to said proximal end for said driver to be slide-ably received within said bore when said cartridge is coupled to said handle.

18. A cartridge kit according to claim 14 wherein said handle has a handle coupling having a predetermined geometry, each of said cartridges further comprising:
   a cartridge coupling at said proximal end of said cartridge and having a mating geometry to mated with said predetermined geometry with said cartridge and handle aligned for said implant to be ejected from said distal tip upon actuation of said actuator.

19. A cartridge kit according to claim 18 further comprising a release for releasing said cartridge from said handle.

20. A cartridge kit according to claim 14 wherein said implant is adapted to alter a dynamic response of said tissue following placement of said implant in said tissue.

21. A cartridge kit according to claim 14 wherein said implant includes a material for promoting tissue in-growth into said implant following placement of said implant into said tissue.

22. A cartridge kit according to claim 14 wherein said implant is sized slightly greater than said bore for said implant to expand upon ejection from said bore.

23. A cartridge kit according to claim 21 wherein said implant is formed of multiple fibers including fibers of said material for promoting tissue in-growth.

24. A cartridge kit according to claim 23 wherein the multiple fibers are twisted together along a length of the implant with the fibers having terminal ends at opposite ends of the implant.

25. A cartridge kit according to claim 23 wherein the multiple fibers are braided together.

26. A cartridge kit according to claim 23 wherein said cartridge is container is sterile.

27. A cartridge according to claim 1, wherein the proximal end of the cartridge includes a plurality of raised gripping elements.

* * * * *